United States Patent [19]
Sachdeva et al.

[11] Patent Number: 5,312,247
[45] Date of Patent: May 17, 1994

[54] TRANSPALATAL ORTHODONTIC APPLIANCE OF SUPERELASTIC OR SHAPE-MEMORY ALLOY

[75] Inventors: Rohit C. L. Sachdeva, Plano, Tex.; Farrokh Farzin-Nia, Inglewood, Calif.

[73] Assignee: Ormco Corporation, Glendora, Calif.

[21] Appl. No.: 887,362

[22] Filed: May 21, 1992

[51] Int. Cl.$^5$ .............................................. A61C 3/00
[52] U.S. Cl. .......................................... 433/7; 433/18
[58] Field of Search ............... 433/7, 18, 19, 20, 21, 433/24

[56] References Cited

U.S. PATENT DOCUMENTS

| | | | |
|---|---|---|---|
| 3,162,948 | 12/1964 | Gerber | 32/14 |
| 3,792,529 | 2/1974 | Goshgarian | 32/14 A |
| 4,037,324 | 7/1977 | Andreasen | 32/14 A |
| 4,197,643 | 4/1980 | Burstone et al. | 433/20 |
| 4,373,913 | 2/1983 | McAndrew | 433/7 |
| 4,433,956 | 2/1984 | Witzig | 433/7 |
| 4,490,112 | 12/1984 | Tanaka et al. | 433/20 |
| 4,592,725 | 6/1986 | Goshgarian | 433/7 |
| 4,815,968 | 3/1989 | Keller | 433/7 |
| 4,818,226 | 4/1989 | Berendt et al. | 433/20 |
| 4,849,032 | 7/1989 | Kawaguchi | 148/11.5 R |
| 4,886,451 | 12/1989 | Cetlin | 433/7 |
| 4,897,036 | 1/1990 | Kesling | 433/18 |
| 4,900,251 | 2/1990 | Andreasen | 433/20 |
| 4,909,735 | 3/1990 | Wildman | 433/24 |
| 4,976,614 | 12/1990 | Tepper | 433/18 |
| 5,011,406 | 4/1991 | Wildman | 433/24 |
| 5,017,133 | 5/1991 | Miura | 433/20 |
| 5,018,969 | 5/1991 | Andreiko et al. | 433/20 |
| 5,044,947 | 9/1991 | Sachdeva et al. | 433/20 |
| 5,046,948 | 9/1991 | Miura | 433/21 |
| 5,131,843 | 7/1992 | Hilgers et al. | 433/20 |
| 5,137,446 | 8/1992 | Yamauchi et al. | 433/21 X |
| 5,167,499 | 12/1992 | Arndt et al. | 433/7 |
| 5,167,500 | 12/1992 | Miura | 433/7 |

FOREIGN PATENT DOCUMENTS 990685 9/1951 France.
1101 of 1869 United Kingdom.

OTHER PUBLICATIONS

An Evaluation of 55 Cobalt Substituted Nitinol Wire For Use In Orthodontics, G. F. Andreasen et al., Jun., 1971, pp. 1373-1375.
Application of Shape Memory Nickel-Titanium Alloys to Orthodontics R. Sachdeva et al., 1989, pp. 605-610.

Primary Examiner—Gene Mancene
Assistant Examiner—Nicholas D. Lucchesi
Attorney, Agent, or Firm—Wood, Herron & Evans

[57] ABSTRACT

Transpalatal orthodontic appliances are disclosed which utilize a shape-memory or superelastic alloy member as the force-supplying member of the device. Suitable alloys include the nickel-titanium (NiTi) alloys, the titanium-molybdenum alloys (TMA), and any other alloy composition which possesses superelastic or shape-memory characteristics. The alloy composition may preferably have a working rang of at least about 30% and a modulus of elasticity not exceeding about $15 \times 10^6$ psi.

29 Claims, 3 Drawing Sheets

TRANSPALATAL ORTHODONTIC APPLIANCE OF SUPERELASTIC OR SHAPE-MEMORY ALLOY

FIELD OF THE INVENTION

The present invention relates to transpalatal appliances for expanding or contracting the maxillary or mandibular arch in an orthodontic patient.

BACKGROUND OF THE INVENTION

Orthodontic appliances are known for repositioning teeth so as to achieve optimum formation of the maxillary and mandibular dental arches. Sometimes expansion of the dental arches is required and other times contraction thereof is required. Orthodontic archwires are used to move teeth, but are not generally suitable to expand or constrict a dental arch. This may be accomplished using transpalatal arches or expansion or constriction appliances.

One such device, the transpalatal arch bar, can be used to expand or contract the dental arches and to rotate, intrude, extrude and/or torque particular teeth in a patient. Transpalatal arch bars and similar related appliances are shown in U.S. Pat. Nos. 3,792,529, 4,592,725, 4,815,968 and 4,886,451. These devices are typically formed of relatively stiff (high modulus of elasticity) stainless steel wire having a U-shaped loop segment or a torsion-spring coil convolution, to supply the desired corrective forces. One drawback associated with such devices is that the spring-like forces supplied by the device are initially high but decrease a the expansion takes place and thus the device must be re-adjusted or replaced at periodic intervals until the desired tooth movement has been achieved.

Another type of device known for correcting transverse dental arch discrepancy is the rapid palatal expander (RPE). Such devices may be used to expand the maxillary arch. The device is affixed, i.e., either bonded or banded, to opposing teeth in the maxillary arch, typically first molars and/or first bicuspids. The transpalatal portion of the device has an expansion screw which the patient turns a predetermined amount each day. Turning the expansion screw in the palatal expander supplies the expansive forces of the device. As with the transpalatal arch bar, the initial force is high, but rapidly decreases as the teeth are moved.

Rapid palatal expanders have several drawbacks, including one or more of the following. The device provides a single force which tends to tip teeth. The forces exerted may be initially as high as 11 lbs., which causes tissue destruction and patient discomfort. Since the devices are patient activated, the cooperation of the patient is required, as is proper training. Furthermore, these devices tend to be bulky and therefore obtrusive to the tongue, which may affect speech and which may adversely affect oral hygiene. Additionally, these devices cannot be fabricated at chair side by the clinician.

SUMMARY OF THE INVENTION

The present invention is directed to transpalatal orthodontic appliances which overcome or obviate the drawbacks associated with prior art devices as described above.

Generally, transpalatal orthodontic appliances according to the present invention are useful for moving teeth (expanding or contracting) in the maxillary or mandibular arches, expanding the dental arches, and may be capable of opening the midpalatal suture in a patient. These results are achieved in a non-obtrusive manner by utilizing a shape-memory or superelastic alloy, such as nickel-titanium type (NiTi) or Beta titanium type (TMA), as the force-supplying member in the transpalatal device which supplies substantially constant corrective forces until the desired tooth movement or arch expansion or contraction is achieved.

The devices may be configured and provided with built-in torque and rotation control so that the corrective forces translate the teeth rather than tip them, which is generally undesirable. Furthermore, tooth displacement in the range of about 0–20 mm can be achieved, which is a significantly greater range than that achievable with known rapid palatal expanders, which typically have a maximum displacement of approximately 12 mm.

Transpalatal orthodontic appliances of the present invention include a force-supplying member of superelastic or shape-memory alloy which may be any suitable composition, so long as the modulus of elasticity of the material does not exceed about $15 \times 10^6$ psi. Additionally, it is desired that the material used has a working range of at least 30%. The use of materials of this type results in a substantially constant corrective force. Although the magnitude of the force will vary depending upon the particular alloy composition used, it will be typically much lower than the forces generated in known rapid palatal expansion devices, and it will be relatively substantially constant as compared to stainless steel devices. By way of comparison, stainless steels used in known transpalatal arch devices typically have a modulus of elasticity in the range of about $25-31 \times 10^6$ psi and a working range of about 15%. such devices are not believed to exert relatively constant corrective forces, can readily deform during usage and have a limited working range.

The appliances of the present invention have several significant advantages. The lower but constant magnitude forces tend not to be destructive to the tissues in and around the dentition and dental arches. The devices will not readily deform and have a substantially greater working range. The devices do not require patient activation or cooperation, and since they are not cumbersome, oral hygiene is facilitated. An additional advantage of the appliances of the present invention is the applicability to virtually any pair or group of teeth in a dental arch. Moreover, two or more appliances may be used concurrently on different sets of teeth to achieve a desired result in tooth positioning and dental arch orientation. When two devices are used, they may exert corrective forces in the same direction, opposite directions, and/or they may exert corrective forces of different magnitudes.

Shape memory or superelastic alloys are known per se and have been used as or in connection with orthodontic arch wires, as described in U.S. Pat. Nos. 4,037,324, 4,197,643, 4,490,112, 4,900,251, 4,976,614, 5,017,133, 5,018,969, and 5,044,947. Such alloys have not been used in transpalatal orthodontic appliances.

The specific alloy composition is not critical to the present invention; however, the alloy must possess shape-memory or superelastic properties, and it preferably has an austenitic transformation temperature ($A_f$) in the range of about −40° to +60° C. Known superelastic and shape-memory alloys are deformable when in the martensitic state (i.e., below the transformation temperature) and possess mechanical memory which returns the material to its original predeformation configuration when heated above the transformation temperature. By way of example only, various NiTi, TMA and other alloys are suitable for use in the present invention.

As used herein, the terms shape-memory and superelastic alloys are intended to include all suitable alloy compositions which possess shape-memory or superelastic properties and which have a modulus of elasticity not exceeding about $15 \times 10^6$ psi and a working range of at least about 30%. Moreover, the term superelastic is intended to mean the ability of a wire to recover at least twice as much as stainless after deformation (bending). For example, stainless steel wire may recover approximately 17% after 90° bending, whereas a superelastic wire of the same diameter should recover approximately 33%.

The present invention utilizes the properties of shape-memory or superelastic alloys in a transpalatal orthodontic appliance to provide substantially constant corrective forces. Since the devices include a force-supplying member of a shape-memory or superelastic alloy which is relatively ductile, the clinician can easily shape or otherwise manipulate the appliance for placement while the alloy is in its martensitic state. Once in place in a patient's mouth, the appliance is activated, as by heating the shape-memory alloy member above its transformation temperature. This activates the mechanical memory of the alloy, causing it to return to a predetermined configuration, thereby imparting desired corrective forces (either expansive or contractive) to the teeth to which it is attached.

In one embodiment, the orthodontic appliances of the present invention may be generally in the form of a transpalatal arch bar consisting entirely of a shape-memory or superelastic alloy. In this embodiment, the terminal segments of the arch bar, which are attached to brackets on the patient's teeth, may be pre-stressed or pre-torqued to counteract tipping the teeth due to the expansive or contractive forces, imparted by the appliance. The term "transpalatal arch bar" as used herein is intended to include a variety of configurations, several examples of which are shown in the figures herein and described hereinbelow.

In an alternative embodiment orthodontic appliances of the present invention include a superelastic or shape-memory alloy member for supplying corrective forces, and further include a rigid structure (e.g., stainless steel) at the terminal ends thereof for connection to the teeth. Appliances of this configuration provide the advantages of a force-supplying member of shape-memory or superelastic alloy, and the rigidity of stainless steel at the points of connection to the patient's teeth.

In still another alternative embodiment, orthodontic appliances of the present invention include a transpalatal spring member of superelastic or shape-memory alloy and are designed to provide contractive forces on selected teeth.

These and other features and advantages of the present invention will become apparent to persons of ordinary skill in the art upon reading the detailed description of the invention in connection with the drawings.

DETAILED DESCRIPTION OF THE INVENTION

Transpalatal orthodontic appliances of the present invention contemplate a variety of configurations, all of which include a force-supplying member of a low modulus, shape-memory or superelastic alloy. Examples, of suitable alloys include nickel-titanium alloys in various stoichiometric ratios, as disclosed in U.S. Pat. No. 4,037,324. U.S. Pat. No. 5,044,947 discloses a nickel-titanium and copper alloy which may also be suitable for use in the present invention. The disclosures of these patents are hereby expressly incorporated herein by reference.

It will be appreciated that each alloy composition will possess a different shape-memory characteristic, a different transformation temperature ($A_f$), a different modulus of elasticity, and a different working range. Thus, the particular alloy composition to be utilized in the orthodontic appliances of the present invention will be selected based on the desired forces supplied by the appliance upon activation thereof and/or the transition temperature of the alloy. In all embodiments of the present invention, the force-supplying member of the appliance has a predetermined configuration determined by the clinician. Once the appliance is placed in the patient's mouth, the force-supplying member is activated, whereupon the shape-memory characteristic thereof causes the force-supplying member to transform or return to its predetermined configuration, thereby imparting desired expansive or contractive forces to move the patient's teeth to desired positions and/or to expand the midpalatal suture. The forces exerted may be in the range of about 300–3,000 grams.

Figure 1:
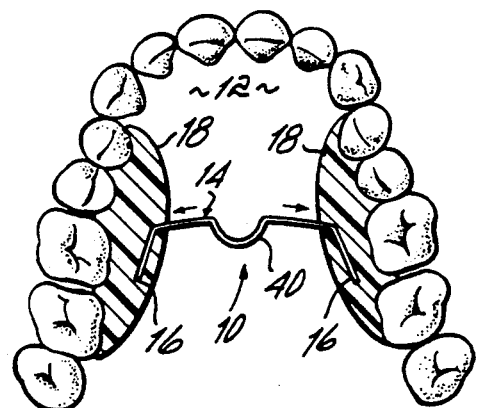
FIG. 1 is a plan view of an upper dental arch with an orthodontic appliance embodying the present invention mounted therein.

With reference to the drawings, FIGS. 1–4 and 8–15 show various alternative embodiments of orthodontic appliances of the present invention. FIG. 1 shows appliance 10 mounted in the upper dental arch 12 of a patient. Appliance 10 comprises a trans-palatal arch bar member 14 made of a shape-memory or superelastic alloy. Shape-memory or superelastic alloy member 14 supplies the desired corrective forces to the teeth in a dental arch upon activation thereof. The corrective forces are substantially constant and ar exerted along substantially a single axis in generally opposed directions. In this particular embodiment, member 14 has its terminal ends 16 embedded in teeth-abutting members 18 which may be acrylic or other suitable material. Teeth-abutting members apply the corrective forces supplied by member 14 to several teeth on opposite sides of the dental arch. This serves to expand the palate of the patient by moving the teeth outwardly and expanding the arch, and may have the capability of opening the midpalatal suture.

Figure 2:
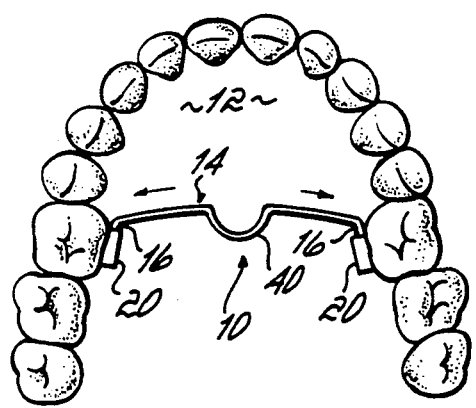
FIG. 2 is a plan view of an upper dental arch with an orthodontic appliance of the present invention mounted therein.

In an alternative embodiment shown in FIG. 2, terminal ends 16 of force-supplying transpalatal arch member 14 are coupled directly to the first molars in the dental arch by means of brackets 20 affixed to the teeth. In FIG. 2, the force-supplying member exerts outwardly-directed corrective forces on the teeth to which it is attached.

Figure 3:
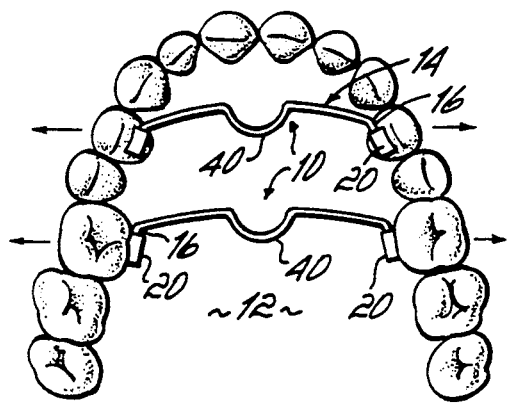
FIG. 3 is a plan view of an upper dental arch with two orthodontic appliances of the present invention mounted therein and exerting corrective forces in the same directions.

FIG. 3 shows a pair of orthodontic appliances 10 in the form of transpalatal arches mounted in a patient's upper dental arch 12. The arrows indicate forces supplied by the transpalatal arches upon activation of the force-supplying members. In this embodiment, both arches 10 provide outwardly-directed expansive forces on the teeth to which they are affixed.

Figure 4:
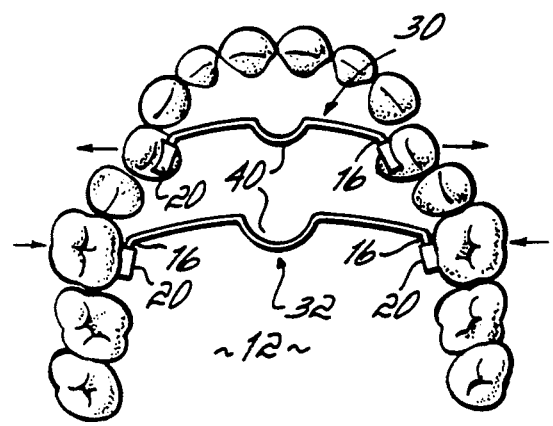
FIG. 4 is a plan view of an upper dental arch with two orthodontic appliances of the present invention mounted therein and exerting corrective forces in opposite directions.

FIG. 4 shows another alternative embodiment, similar to that shown in FIG. 3, wherein two transpalatal arches are affixed to different pairs of teeth in the dental arch. In this embodiment, the corrective forces supplied are generally in opposite directions, as indicated by the arrows. More particularly, upon activation of the force-supplying members, transpalatal arch 30 exerts expansive forces on the first bicuspids and transpalatal arch 32 concurrently exerts contractive forces on the first molars. With this combination of appliances, and variations thereof, virtually any desired tooth or arch manipulation can be achieved.

It will be appreciated that in embodiments of the present invention such a those shown in FIGS. 3 and 4, the corrective forces supplied by the transpalatal arches may be in the same or opposite directions. It will also be appreciated that forces of substantially the same or different magnitudes may be supplied, depending on the required tooth or arch manipulation.

Figure 8A:
FIGS. 8A and 8B show an alternative embodiment of a orthodontic appliance of the present invention before and after activation, respectively.
Figure 8B:
Figure 9A:
FIGS. 9A and 9B show another alternative embodiment of an orthodontic appliance of the present invention before and after activation, respectively.
Figure 11A:
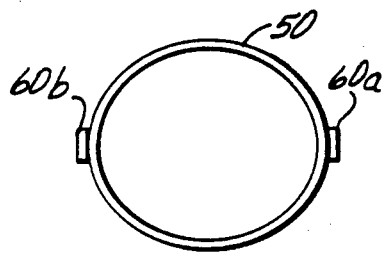
FIGS. 11A and 11B show another alternative embodiment of the present invention before and after activation, respectively.
Figure 9B:
Figure 10A:
FIGS. 10A and 10B show another alternative embodiment of the present invention before and after activation, respectively.
Figure 11B:
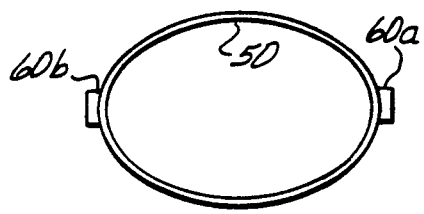
Figure 10B:

In the embodiments shown in FIGS. 1–4, the force-supplying members in the orthodontic appliances comprise a transpalatal arch which includes a U-shaped, spring-like section 40. Various alternative configurations of the transpalatal arch will be apparent to persons of ordinary skill in the art. Several contemplated alternatives are shown in FIGS. 8–11. The transpalatal arch shown in FIGS. 8A and 8B has a zig-zag configuration. FIG. 8A shows a plan view of the arch prior to activation and FIG. 8B shows the arch subsequent to activation. In FIGS. 9A and 9B, the transpalatal arch consists of continuous S-shaped curves. FIG. 9A shows the arch prior to activation and FIG. 9B shows the arch subsequent to activation. FIGS. 10A and 10B, respectively, show a frontal view of a transpalatal arch with a U-shaped medial segment in its pre- and post-activation configurations. Finally, FIGS. 11A and 11B show an embodiment of the present invention wherein the force-supplying member is generally in the shape of a ring 50 having bracket members 60a and 60b on diametrically opposite sides thereof for attachment to the desired teeth in the dental arch. FIG. 11A shows ring member 50 prior to activation and FIG. 11B shows ring member 50 subsequent to activation.

Figure 6:
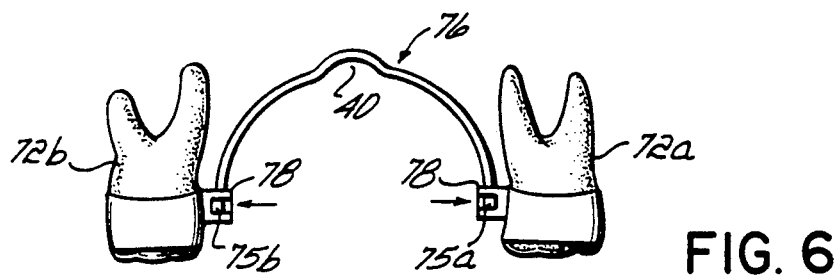
FIG. 6 is a side elevational view of a patient's upper first permanent molars with an orthodontic appliance of the present invention mounted thereon.
Figure 5:
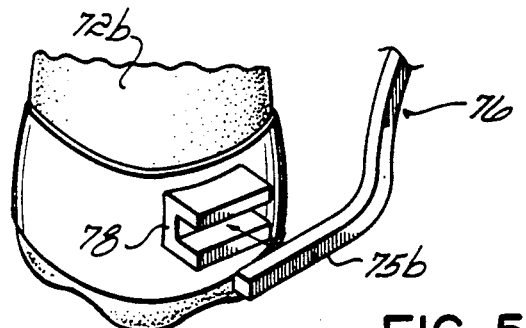
FIG. 5 is a perspective view, partially broken away, illustrating the interfit between the terminal portion of a dental appliance of the present invention and an orthodontic bracket mounted to a tooth.
Figure 7:
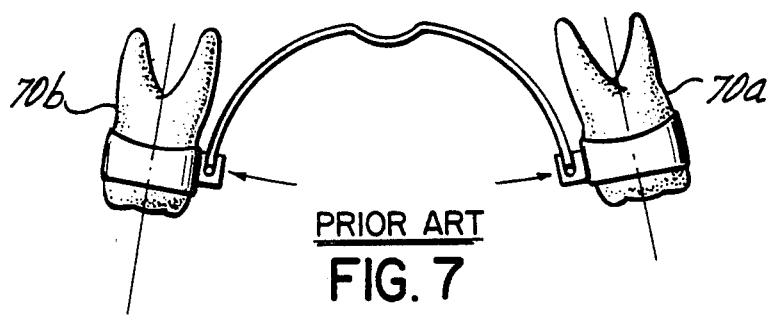
FIG. 7 is a side elevational view similar to FIG. 6 but showing the effects of a prior art transpalatal arch bar mounted on a patient's teeth.

FIG. 7 illustrates one drawback associated with some prior art transpalatal arches. Due to the nature of the forces exerted by stainless steel or other relatively high modulus materials, i.e., an initially high force which rapidly decreases, the teeth 70a and 70b to which the arch is affixed may be tipped, as shown in FIG. 7. In many instances this tipping or torquing of the teeth is undesirable and may occur to the exclusion of the desired translating movement of the teeth. The tipping must then be corrected utilizing a secondary procedure. FIG. 6 shows an embodiment of an orthodontic appliance of the present invention which overcomes the above-described drawback of prior art arches. As shown in FIGS. 5 and 6, terminal portions 75a and 75b of orthodontic appliance 76 are pre-torqued or pre-stressed to counteract the tendency of the expansive forces to tip teeth 72a and 72b. FIG. 5 shows terminal portion 75b of orthodontic appliance 76 as it is fitted into cooperation with bracket 78 attached to tooth 72b. Pre-torquing the terminal portion 75b may be accomplished by twisting the terminal portion from a predetermined configuration such that upon activation thereof it returns to its predetermined configuration, thereby counteracting any torquing or tipping forces applied to the teeth by transpalatal arch 76.

Figure 12:
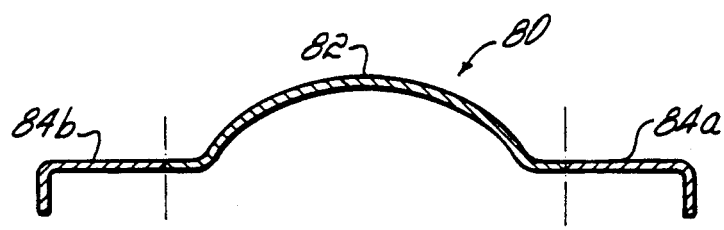
FIG. 12 is a cross-sectional view of an alternative embodiment of an orthodontic appliance of the present invention.

In an alternative embodiment shown in FIG. 12, an orthodontic appliance 80 of the present invention includes a force-supplying, superelastic or shape-memory alloy member 82 with rigid structure at its terminal ends 84a, 84b for attachment to a patient's teeth.

More particularly, FIG. 12 shows a transpalatal arch 80 comprising a medial shape-memory alloy segment 82 and terminal end segments 84a and 84b of stainless steel or other relatively rigid material. Since the generally U-shaped medial segment 82 is a shape-memory alloy, it supplies substantially constant corrective forces upon activation. This embodiment is advantageous when more rigid structure is required at the point of connection to the patient's teeth.

Figure 13:
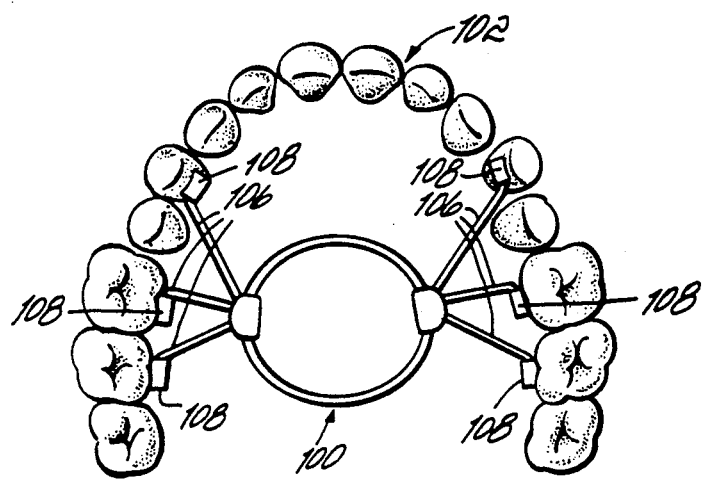
FIG. 13 is a plan view of an upper dental arch with an orthodontic appliance of the present invention mounted therein.

FIG. 13 shows an alternative embodiment of an orthodontic appliance comprising a shape-memory alloy member for supplying the corrective forces and rigid structure for attachment to the teeth. Orthodontic appliance 100 is shown in FIG. 13 affixed to several teeth in an upper dental arch 102. Appliance 100 comprises a force-supplying member 104 in the form of a ring of superelastic or shape memory alloy. Appliance 100 further comprises a plurality of relatively rigid legs 106 (e.g., stainless steel) which transmit the forces supplied by ring 104 to the teeth in the dental arch to which they are affixed, as by brackets 108.

Figure 14:
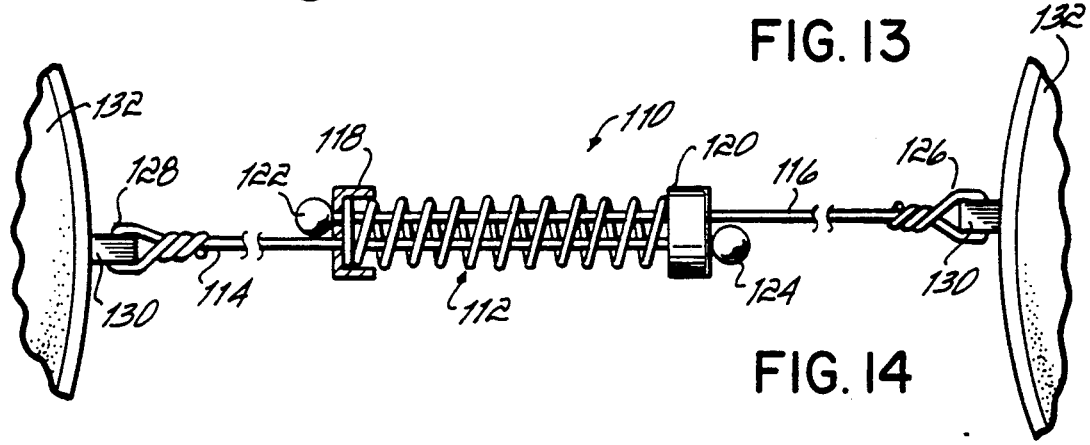
FIG. 14 is a plan view, partially broken away, of an alternative embodiment of an orthodontic appliance of the present invention mounted to a patient's teeth.
Figure 15:
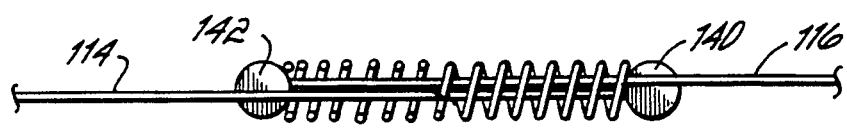
FIG. 15 is a plan view, partially broken away, of an alternative embodiment of the appliance of FIG. 14.

FIGS. 14 and 15 show additional alternative embodiments of an orthodontic appliance of the present invention. This particular embodiment is suitable for providing contractive forces (or, with design modifications, expansive forces) on selected teeth in a dental arch. As shown in FIG. 14, appliance 110 includes a coil spring 112 of superelastic or shape-memory alloy and first and second ligation wires 114 and 116, respectively. Appliance 110 also includes a pair of end caps 118, 120 designed to receive the terminal ends 122, 124, respectively, of first and second ligation wires 114 and 116, such that coil spring 112 is captured therebetween.

In the particular embodiment illustrated, each of the end caps 118, 120 has a generally cupshaped configuration for receiving a respective terminal end of spring 112. Associated with each end cap 118, 120 are first and second ligature wires, 114, 116, respectively. Terminal ends 122, 124 of ligature wires 114, 116 are sized and configured such that they will not pass through the openings in the end caps. As shown in FIG. 14, the terminal ends 122 and 124 comprise an enlarged bulbous section which is integrally formed at the end of the wire. However, it is to be understood that the terminal ends may be formed in any desired manner; the only requirement is that the terminal ends of the wires 114, 116 not pass through the openings in the end caps. The free end 126, 128 of each ligature wire is used to ligate the appliance to the appropriate orthodontic brackets 130 that have been affixed to teeth 132 in the patient's mouth.

When appliance 110 is ligated to brackets 130, coil spring 112 is in compression. Upon activation of the shape-memory or superelastic alloy spring 112, it tends to expand, thereby exerting expansive forces outwardly against end caps 118, 120, which, in turn, apply contractive forces on teeth 132 via ligating wires 114, 116. The size, shape and alloy composition of coil spring 112 are selected to provide the desired contractive forces.

The orthodontic appliance embodiment shown in FIG. 15 is similar to that shown in FIG. 14. In FIG. 15, the ligature wires 114, 116 have disks 140, 142 affixed to their terminal ends. Disks 140, 142 are sufficiently large in diameter that they will not pass through coil spring 112, thus obviating the need for end caps These spring-/ligature combinations may also be used as Class II, Class III, space closure and headgear devices or for correction of tooth discrepancies relative to one another.

While the orthodontic appliances of the present invention have been described with reference to the drawings, the scope of the present invention is not intended to be limited to the particular examples shown or described. It is contemplated that variations in design will be apparent to persons skilled in the art. Therefore, the scope of the present invention is defined by the appended claims.

What is claimed is:

1. A transpalatal orthodontic appliance comprising: a transpalatal force-supplying member of shape-memory or superelastic alloy having a substantially longitudinal axis and including a pair of terminal ends for connection to corresponding opposed teeth in a dental arch of a patient, said member having a predetermined activation temperature and a predetermined configuration, said member transforming to said predetermined configuration upon activation, wherein said member comprises means for exerting during transformation substantially constant corrective forces on said teeth in a dental arch along said longitudinal axis of said member.

2. A transpalatal orthodontic appliance of claim 1 wherein said transpalatal force-supplying member is in the form of a transpalatal arch wire member and further comprising means for connecting said terminal ends of said transpalatal arch wire member to said corresponding opposed teeth in a dental arch of a patient.

3. A transpalatal orthodontic appliance of claim 2 wherein said arch wire member has a cross-sectional shape which cooperates with said connecting means and upon activation transfers and applies a torsional force to at least one of said teeth to which it is connected to counteract any tipping of said at least one of said teeth resulting from the corrective force applied to the tooth.

4. A transpalatal orthodontic appliance of claim 3 wherein said cross-sectional shape of said arch wire member is substantially rectangular.

5. A transpalatal orthodontic appliance of claim 1 wherein said corrective forces are applied in generally opposed directions which cause the dental arch to be expanded.

6. A transpalatal orthodontic appliance of claim 1 wherein said corrective forces are applied in generally opposed directions which cause the dental arch to be constricted.

7. A transpalatal orthodontic appliance according to claim 1 wherein said corrective forces are in the range of about 300–3,000 grams.

8. A transpalatal orthodontic appliance of claim 7 wherein said appliance can achieve active displacement in said dental arch of up to about 20 mm.

9. A transpalatal orthodontic appliance of claim 1 wherein said force-supplying member comprises a nickel-titanium based alloy.

10. A transpalatal orthodontic appliance of claim 1 wherein said force-supplying member comprises a titanium-molybdenum based alloy.

11. A transpalatal orthodontic appliance of claim 1 wherein said force-supplying member comprises an alloy having modulus of elasticity not exceeding about $15 \times 10^6$ psi.

12. A transpalatal orthodontic appliance of claim 1 wherein said force-supplying member comprises an alloy having a working range of at least about 30%.

13. A transpalatal orthodontic appliance of claim 1 wherein said predetermined activation temperature is about body temperature.

14. A transpalatal orthodontic appliance of claim 1 wherein said transpalatal force-supplying member is a superelastic alloy having an activation temperature in the range of about −40° C. to +60° C.

15. A transpalatal orthodontic appliance of claim 1 wherein said transpalatal force-supplying member is in the form of a transpalatal arch wire having terminal ends, each said terminal end having affixed thereto a member for abutting at least one tooth in a dental arch, said members abutting and imparting corrective forces on corresponding opposed teeth in the dental arch.

16. A transpalatal orthodontic appliance of claim 15 wherein said abutting members exert substantially constant corrective forces on said opposed teeth in generally opposed directions.

17. A transpalatal orthodontic appliance of claim 16 wherein said abutting members are affixed to said opposed teeth and said corrective forces cause the dental arch to be expanded.

18. A transpalatal orthodontic appliance of claim 17 wherein said corrective forces are in the range of about 300–3,000 grams.

19. A transpalatal orthodontic appliance of claim 18 wherein said appliance can achieve displacement in said dental arch of up to about 20 mm.

20. A transpalatal orthodontic appliance comprising:
first and second transpalatal force-supplying members of shape-memory or superelastic alloy, each member having a substantially longitudinal axis and including a pair of terminal ends for connection to corresponding opposed teeth in a dental arch of a patient, each said member having a predetermined activation temperature and a predetermined configuration, said members transforming to said predetermined configuration upon activation, wherein substantially constant corrective forces along its respective longitudinal axis and on said teeth in a dental arch.

21. A transpalatal orthodontic appliance of claim 20 wherein said transpalatal force-supplying members are in the form of transpalatal arch wire members and further comprising means for connecting said terminal ends of said arch wire members to said corresponding opposed teeth in a dental arch of a patient.

22. A transpalatal orthodontic appliance of claim 21 wherein said first arch wire member and said second arch wire member exert corrective forces which cause the dental arch and midpalatal suture to be expanded.

23. A transpalatal orthodontic appliance of claim 22 wherein said corrective forces exerted by said first and second arch wire members are of substantially the same magnitude.

24. A transpalatal orthodontic appliance of claim 22 wherein said corrective forces exerted by said first and second arch wire members are of different magnitudes.

25. A transpalatal orthodontic appliance of claim 21 wherein said first arch wire member and said second arch wire member exert corrective forces which cause the dental arch to be constricted.

26. A transpalatal orthodontic appliance of claim 25 wherein said corrective forces exerted by said first and second arch wire members are of substantially the same magnitude.

27. A transpalatal orthodontic appliance of claim 25 wherein said corrective forces exerted by said first and second arch wire members are of different magnitudes.

28. A transpalatal orthodontic appliance of claim 21 wherein said corrective force exerted by said first arch wire member causes the distance between the teeth to which it is connected to be expanded, and said corrective force exerted by said second arch wire member causes the distance between the teeth to which it is connected to be constricted.

29. A transpalatal orthodontic appliance of claim 21 wherein said corrective force exerted by said first arch wire member causes the distance between the teeth to which it is connected to be constricted, and said corrective force exerted by said second arch wire member causes the distance between the teeth to which it is connected to be expanded.

* * * * *

UNITED STATES PATENT AND TRADEMARK OFFICE
CERTIFICATE OF CORRECTION

PATENT NO. : 5,312,247
DATED : May 17, 1994
INVENTOR(S) : Rohit C. L. Sachdeva et al.

It is certified that error appears in the above-indentified patent and that said Letters Patent is hereby corrected as shown below:

In the Abstract, at line 8, "rang" should be --range--.

At column 1, line 31, "a" should be --as--.

At column 5, line 20, "ar" should be --are--.

At column 5, line 58, "a" should be --as--.

At column 9, line 2, after "wherein" and before "substantially", please insert --each of said members comprises means for exerting during transformation--.

Signed and Sealed this

Twenty-seventh Day of September, 1994

Attest:

BRUCE LEHMAN

*Attesting Officer*   *Commissioner of Patents and Trademarks*